United States Patent
Nakano et al.

(12)

(10) Patent No.: US 6,825,437 B2
(45) Date of Patent: Nov. 30, 2004

(54) APPARATUS ENABLING PARTICLE DETECTION UTILIZING WIDE VIEW LENS

(75) Inventors: Hiroyuki Nakano, Yokohama (JP); Takeshi Arai, Yokohama (JP); Toshihiko Nakata, Hiratsuka (JP)

(73) Assignee: Hitachi, Ltd., Tokyo (JP)

( * ) Notice: Subject to any disclaimer, the term of this patent is extended or adjusted under 35 U.S.C. 154(b) by 16 days.

(21) Appl. No.: 10/231,267

(22) Filed: Aug. 30, 2002

(65) Prior Publication Data

US 2003/0054655 A1 Mar. 20, 2003

Related U.S. Application Data

(63) Continuation-in-part of application No. 09/933,185, filed on Aug. 21, 2001, and a continuation-in-part of application No. 09/763,735, filed on Sep. 17, 2001, and a continuation-in-part of application No. 09/791,677, filed on Feb. 26, 2001, and a continuation-in-part of application No. 09/760,704, filed on Jan. 17, 2001.

(51) Int. Cl.[7] .............................................. B23K 10/00
(52) U.S. Cl. ............................ 219/121.41; 219/121.43; 219/121.54; 204/298.37; 156/345.24; 356/16; 438/7
(58) Field of Search ....................... 219/121.4, 121.41, 219/121.43, 121.36, 121.48, 121.54; 204/298.21, 298.36, 298.37, 298.31; 156/645.1, 646.1, 345.24; 118/723 I; 356/706–714; 438/7, 16, 680–685

(56) References Cited

U.S. PATENT DOCUMENTS

| | | | | |
|---|---|---|---|---|
| 5,343,290 A | * | 8/1994 | Batchelder et al. | 356/349 |
| 5,448,364 A | * | 9/1995 | Moran | 356/430 |
| 5,861,952 A | * | 1/1999 | Tsuji et al. | 356/349 |
| 5,936,726 A | * | 8/1999 | Takeda et al. | 356/237.2 |
| 5,943,130 A | * | 8/1999 | Bonin et al. | 356/336 |
| 6,052,183 A | * | 4/2000 | Lee | 356/337 |
| 6,346,425 B1 | * | 2/2002 | Ito et al. | 438/7 |

\* cited by examiner

*Primary Examiner*—Mark Paschall
(74) *Attorney, Agent, or Firm*—Antonelli, Terry, Stout & Kraus, LLP

(57) ABSTRACT

When determining the presence of foreign particles in a processing chamber by radiating a laser beam inside a processing chamber and detecting scattered light from foreign particles within the processing chamber, the detection of scattered light is performed using a detecting lens having a wide field angle and deep focal depth. Accordingly, the detection of foreign particles floating in the processing chamber can be performed across a wide range, and with uniform sensitivity, with a detecting optical system having a simple constitution.

31 Claims, 14 Drawing Sheets

APPARATUS ENABLING PARTICLE DETECTION UTILIZING WIDE VIEW LENS

CROSS REFERENCE TO RELATED APPLICATION

This is a continuation-in-part of U.S. application Ser. No. 09/763,735, filed Sep. 17, 2001, U.S. application Ser. No. 09/760,704, filed Jan. 17, 2001, U.S. application Ser. No. 09/791,677, filed Feb. 26, 2001, and U.S. application Ser. No. 09/933,185, filed Aug. 21, 2001, the subject matter of which is incorporated by reference herein.

BACKGROUND OF THE INVENTION

The present invention relates to a semiconductor processing method, for use in the formation of semiconductor substrates or liquid crystal substrates, and its apparatus; and, more particularly, the invention relates to a semiconductor processing method and its apparatus, which are provided with a function for in situ measurement of foreign particles floating within a processing chamber that serves for performing processes, such as the formation of thin films (film growth) and etching, and which are capable of determining the state of contamination of the processing chamber.

Processes using plasma, such as those performed in an etching apparatus, are widely applied in the manufacture of semiconductor devices and substrates for liquid crystal display apparatuses.

An example of an apparatus using a plasma process is a plasma etching apparatus. In such a plasma etching apparatus, the reaction products produced by the etching reaction with the plasma accumulate on the walls of the plasma processing chamber or the electrodes, and as time passes these accumulated reaction products separate and become floating particles. These floating particles can drop onto the wafer at the instant when the etching process is finished and the plasma discharge is stopped, so as to become adhered particles, resulting in bad circuits and a bad pattern appearance. In the end, these particles become a factor in a low product yield and a reduced reliability of the elements.

A great many apparatuses for detecting foreign particles that have adhered on the wafer surface in the above-mentioned manner have been reported and are being applied, but these apparatuses perform an inspection under conditions where the wafer is removed from the plasma processing apparatus. At that time, when it is determined that most foreign particles will occur, the processing of another wafer is already under way, and a problem results in the form of a reduced yield, because of the large volume of bad wafers that are produced. Also, in the evaluation after the process, the distribution of the occurrence of foreign particles within the processing chamber and the change in conditions over time are not determined.

Consequently, a technique for providing real-time, in situ, monitoring of the state of contamination within a processing chamber is in demand in various technical fields, such as semiconductor manufacture and liquid crystal device manufacture. The size of the particles floating within the processing chamber is in the sub-micron to several hundred micrometer range. In the semiconductor field, where densification is progressing to provision of a 256 Mbit DRAM (dynamic random access memory) and a 1 Gbit DRAM, the minimum line width of a circuit pattern is 0.25 to 0.18 $\mu$m and is progressively getting smaller. Thus, the size of the particles to be detected must also be on the order of a sub-micron.

The conventional techniques for monitoring foreign particles floating within a processing chamber (vacuum processing chamber), such as a plasma processing chamber, include the technologies disclosed in Japanese Patent Laid-open Publications No. H3-25355 (publication 1), H10-213539 (publication 2), H11-251252 (publication 3), and H11-330053 (publication 4).

The above-mentioned publication 1 discloses a microscopic particle measurement apparatus for measuring microscopic particles that have adhered on the semiconductor device substrate surface and microscopic particles that are floating using the scattering of a laser beam. This apparatus includes a laser beam phase modulator for generating two laser beams that are modulated with prescribed frequencies so that the wavelengths thereof are the same, but the phases thereof are different; an optical system for causing the two laser beams to intersect in a space including microscopic particles, which represent the measurement subject; a photodetector for receiving light scattered by the microscopic particles in the region where the two laser beams intersect and converting the light to an electrical signal; and a signal processor for extracting a signal component, wherein the phase modulation signal and frequency in the laser beam phase modulator are the same or double in the electrical signal from this scattered light, and the phase difference between the phase modulated signals is constant over time.

The above-mentioned publication 2 makes note of a microparticle sensor that includes a beam emitter for emitting a beam of light so as to radiate the beam across a measured volume; a detector, including a photodetector, and an optical system for focusing the scattered light from the measured volume and directing that light to the photodetector, whereby the photodetector generates a signal representing the intensity of the light directed to the photodetector; and signal processing means having a pulse detector which is connected so as to analyze the signal from the photodetector and detect pulses in the signal from the photodetector, and an event detector for the microparticles, which specifies a series of pulses caused by scattered light resulting from the microparticles following irradiation a plurality of times with the above-mentioned beam during the time when those microparticles are moving within the measured volume.

Publications 3 and 4 make note of foreign particle monitoring technology wherein a beam of light, having a desired wavelength and with its intensity modulated by a desired frequency, is radiated within a processing chamber, scattered light attained from within the processing chamber is separated into the desired wavelength component, and collected and converted to a signal; and by the extraction of the intensity modulated component with the desired frequency from that signal, a signal representing the foreign particles floating in or near the plasma is separated and detected from that signal resulting from the plasma. In particular, FIGS. 15 and 16 in publication 3 show an optical system for detecting side-scattered light, which comprises an interference filter, an imaging lens, an optical length correcting prism, a plurality of pinholes, and a parallel output type photodiode array.

However, in the semiconductor field where densification is progressing to provision of a 256 Mbit DRAM and a 1 Gbit DRAM, the minimum line width of the circuit pattern is 0.25 to 0.18 $\mu$m and is progressively getting smaller. Thus, the size of the particles to be detected must also be on the order of a sub-micron.

In the above-mentioned publications 1 and 2, however, the application of the technology is limited to the observation of comparatively large particles, because of the difficulty in separating the particle-scattered light and the plasma emission, and it is believed to be difficult to detect microscopic particles on the order of a sub-micron.

On the other hand, in the above-mentioned publications 3 and 4, the problem is that the detection optical systems are complicated and expensive, even though it is possible to separate the particle-scattered light and the plasma emission. In this regard, a beam of light having the desired wavelength and with its intensity modulated by the desired frequency, is radiated within a processing chamber, and scattered light attained from within the processing chamber is separated into the above-mentioned desired wavelength component, collected and converted to a signal, so that the intensity modulated component with the desired frequency can be extracted from that signal, but the processing is complicated and expensive.

SUMMARY OF THE INVENTION

The present invention is directed to a plasma processing method and an apparatus therefor which provide improved yields, and which makes possible real-time monitoring of the state of contamination in a plasma processing chamber with a simplified detecting optical system, and with greatly improved detection sensitivity for detecting and separating the plasma emission for sub-micron, floating microscopic particles in or near the plasma in a plasma processing chamber.

Also, the present invention is directed to a semiconductor processing method which makes it possible to manufacture high-quality semiconductors with high yields, and which makes possible real-time monitoring of the state of contamination in a plasma processing chamber with a simplified detecting optical system, and with greatly improved detection sensitivity for detecting and separating the plasma emission for sub-micron, floating microscopic particles in or near the plasma in a plasma processing chamber.

Specifically, in accordance with the present invention, when the desired thin film growth or finishing process for a processed substrate (semiconductor substrate) is performed in a processing chamber, for example, when a laser beam from an external laser beam source passes through a viewing window and radiates into the processing chamber, light scattered by foreign particles within the processing chamber is then received by one detecting lens, and from the above-mentioned detection signal, the number, size, and distribution of foreign particles, as well as the state of contamination of the inner walls of the processing chamber, are determined, and the results of this determination are displayed on a display.

Also, the present invention is directed to a semiconductor processing method and plasma processing method having an introduction step of introducing a semiconductor substrate into a processing chamber; a plasma generating step of generating plasma in the processing chamber, a processing step of processing a semiconductor substrate by processing the semiconductor substrate by reaction with the generated plasma in the processing chamber: a foreign particle detection step of detecting foreign particles floating in or near the generated plasma in the processing chamber; and a removal step of removing the processed semiconductor substrate from the processing chamber.

The above-mentioned foreign particle detection step includes a radiation step of radiating a laser beam through a window in the processing chamber and causing the beam to scan over and irradiate the semiconductor substrate in the processing chamber, using a scanning optical system; a detecting step wherein, when the laser beam is scanned over the semiconductor substrate in the radiation step, scattered light from floating foreign particles occurring across the entire region over the semiconductor substrate passes through a window in the processing chamber and is focused on the plane of incidence by a detecting lens, which has a wide field angle, so as to cause the light to be incident to the plane of incidence, and a detecting optical axis different from the illuminating optical axis of the scanning optical system, and the light focused on the plane of incidence is received with a detector and is converted to a first signal; and a step of attaining floating foreign particle information from the first signal.

These and other objects, features and advantages of the invention will be apparent from the following more particular description of preferred embodiments of the invention, as illustrated in the accompanying drawings.

DESCRIPTION OF THE PREFERRED EMBODIMENTS

The present invention provides a plasma processing method and an apparatus therefor, which are designed to make it possible to achieve real-time monitoring of the state of contamination in a plasma processing chamber (in which a specimen is processed by using plasma produced inside said chamber) and to improve the processing yield.

The present invention also provides semiconductor processing method, and an embodiment thereof for use on a production line, which has the characteristic of reducing the number of bad processed substrates (subjects of process) resulting from adhered particles, and which is capable of processing high-quality semiconductor elements or the like. Plasma processing apparatuses for processing semiconductor elements or the like typically include a plasma etching apparatus and a plasma film growth apparatus. These plasma processing apparatuses generate plasma within a processing chamber and perform etching on a substrate, or film growth using CVD and sputtering.

An embodiment for real-time monitoring of the state of contamination (the situation involving the generation of foreign particles or the like) within a processing chamber in these types of plasma processing apparatuses will be explained below with reference to FIGS. 1 through 21 to exemplify the features of the present invention.

Moreover, each of the embodiments relating to the present invention as discussed below represent examples in which the present invention is applied to a parallel plane plasma etching apparatus of the type used in plasma dry etching; however, the scope of the present invention is not limited thereby, and the present invention may also be applied to thin film formation (film growth) apparatuses, such as sputtering apparatuses and CVD apparatuses, or to various types of thin film formation and processing apparatuses, such as ECR etching apparatuses, microwave etching apparatuses, or ashing apparatuses.

Figure 1:
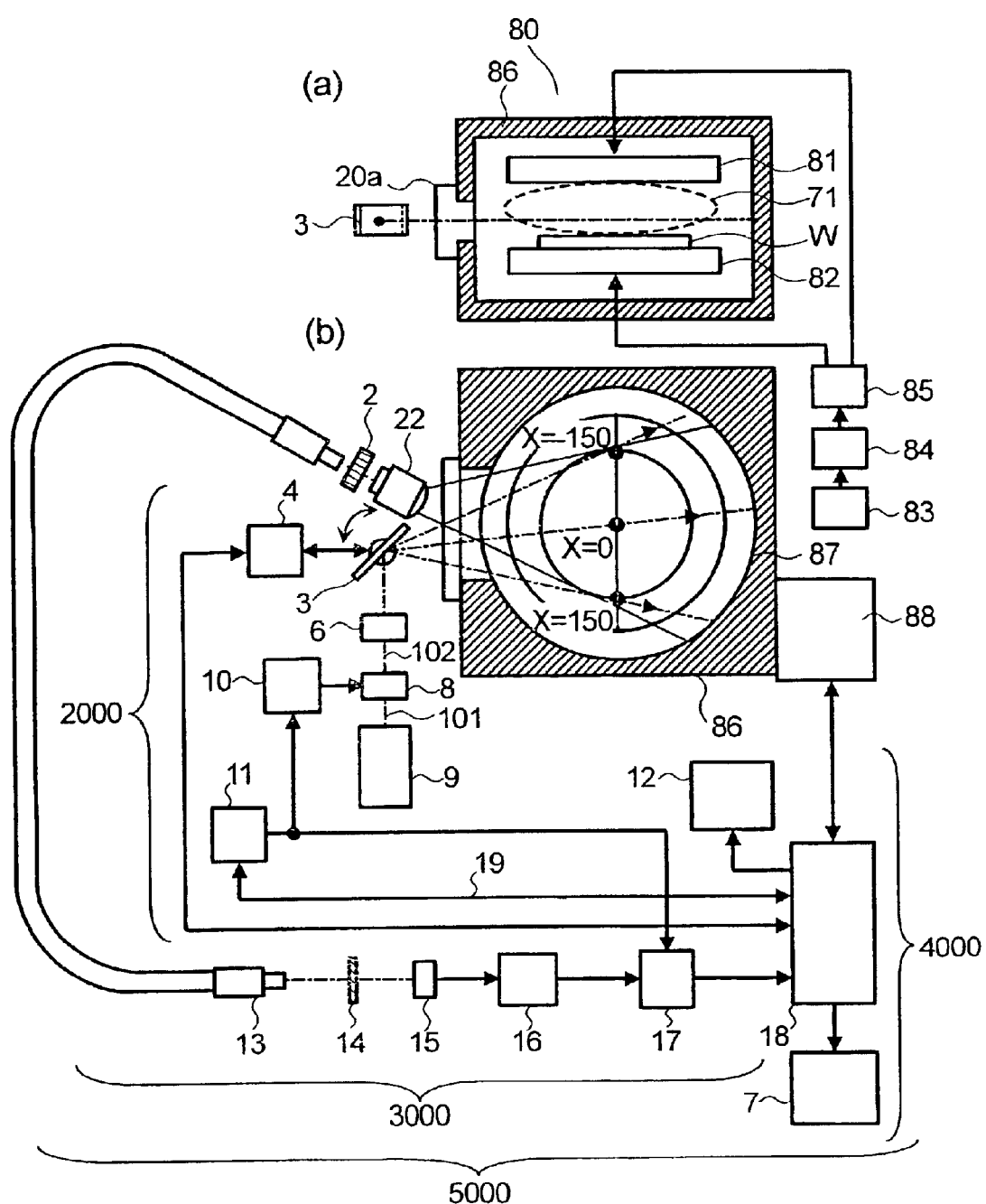
FIGS. 1(a) and 1(b) are schematic diagrams showing a first embodiment of a plasma processing apparatus according to the present invention (an etching process apparatus having a device for measuring floating particles in the plasma)

A plasma processing apparatus relating to a first embodiment of the present invention will be explained with reference to FIGS. 1(a) through 11. As shown in FIG. 1(a), the etching process apparatus 80 generates plasma 71 in the space above an electrode 82 whereon a wafer W rests, so that the wafer W is processed with the plasma being generated. In this plasma processing apparatus, during the course of plasma processing of the wafer W, reaction products are not exhausted, so that some of the products are accumulated on the inner walls of the processing chamber 86 and the electrode 82. Furthermore, as a large number of wafers W undergo plasma processing, much of the accumulated reaction products separate from the surfaces and float in the processing chamber 86, penetrating the plasma 71. Many of those particles adhere to the surface of the wafer W, resulting in the production of a bad processed wafer W onto which a large quantity of foreign particles is adhered. In particular, as the densification of circuit patterns formed on processed wafers progresses in the field of semiconductor manufacture, the minimum line width of a circuit pattern is 0.25 to 0.18 μm and is progressively getting smaller. Consequently, even though the size of the foreign particles that have adhered on the surface of the processed wafer is on the order of a sub-micron, bad processed wafers are produced.

In the etching process apparatus as shown in FIG. 1(a), the output voltage of a power amp 84 is modulated by a high frequency signal received from a signal generator 83, and this high frequency voltage is divided, a splitter 85, and is applied across an upper electrode 81 and lower electrode 82, that are disposed in parallel to each other, in the plasma processing chamber 86. As a result of the discharge across the electrodes, the etching gas supplied to the processing chamber is made into a plasma, so that the plasma 71 is generated. The semiconductor substrate (wafer) W, which is the processing object, is etched with the active species thereof. A 380 to 800 kHz signal is used as the high frequency signal. Furthermore, the etching process apparatus performs an etching process in such a way that a desired pattern formation and depth are achieved by monitoring the progress of the etching and detecting, as accurately as possible, the end point thereof. Specifically, when the end point is detected, the output of the power amp 6 is stopped, and, thereafter, the processed wafer W is transported from the processing chamber 86. Otherwise, the plasma etching apparatus 80 may be of the type which etches by introducing resonating microwaves and creates a plasma with a magnetic field or an electrical field.

The plasma film growth apparatus may be of a type which supplies a CVD gas, for example, creates a plasma of this supplied CVD gas using high frequency power from the upper electrode, and causes a reaction to form films on the processed substrate.

A plasma floating particle measuring apparatus (foreign particle detecting apparatus) 5000 relating to the present invention will be explained next. FIG. 1(b) shows an example of the etching process apparatus having a foreign particle monitor (foreign particle detecting device) for detection of contaminants in the processing chamber, according to the present invention. The apparatus 5000 for measuring foreign particles within the processing chamber comprises mainly a laser radiating optical system 2000, a scattered light detecting optical system 3000, and a control and signal processing system 4000. In a first embodiment of the apparatus 5000 for measuring foreign particles within the processing chamber, the radiated beam outlet in the laser radiating optical system 2000 and the detection beam inlet in the scattered light detecting optical system 3000 are disposed so as to be opposite the viewing window (window glass) 20a provided in the side of the plasma processing chamber 86. Specifically, the scattered light detecting optical system 3000 detects mainly the back-scattered light generated from floating foreign particles by detecting the laser beam passing through the illuminating viewing window (window glass) 20a.

In the laser radiating optical system 2000, a beam 101 that is output from a laser light source 9 (for example, that which outputs a solid laser beam with wavelength 532 nm, a 633 nm He—Ne laser beam, a 514.5 nm Ar laser beam, or a 780 nm semiconductor laser beam) is incident to an intensity modulator 8. The intensity modulator 8 can be constituted of an AO (accousto-optical) modulator or a mechanical intensity modulator, which causes high-speed rotation of a disk having an aperture therein. On the basis of a control signal 19 from the computer 16, a short wavelength signal with a frequency of 170 kHz and duty of 40 to 60% (preferably 50%) is output from an oscillator 11 and is applied to a driver 10 which drives the intensity modulator 8. Thereby, the beam 101 is subjected to intensity modulation at the above-mentioned frequency by the intensity modulator 8. In the present embodiment, where the high frequency voltage applied to the electrode of the etching process apparatus is 400 kHz, the laser intensity modulation frequency may be 400 kHz and the above-mentioned frequency 170 kHz, which is different from the 800 kHz and 1.2 MHz high frequency component thereof. The reason for this will be discussed below.

The intensity modulated beam 102 is focused at the center of the substrate (wafer) by the lens group 6. The beam is reflected by the galvanomirror (scanning optical system) 3 and guided into the processing chamber 86 through the viewing window 20a in the side of the plasma processing chamber 86. Moreover, the lens group 6 may be constituted of an optical system with a focal depth spanning 300 mm and is able to maintain a spot of diameter 10 to 30 μm, as noted in Japanese Patent Laid-open Publication No. 1111-251252, but this becomes expensive.

As the galvanomirror (scanning optical system) 3 is caused to rotate, the beam is scanned in a plane parallel to the surface of the substrate (wafer), and, thereby, it becomes possible to illuminate (detect foreign particles) the area above the entire surface of the substrate (wafer) W. The scanning optical system 3 may be an optical system which can scan a beam in a plane parallel to the wafer surface, but it is not limited to being a galvanomirror. It can also be constituted with a rotating prism, for example.

Figure 2:
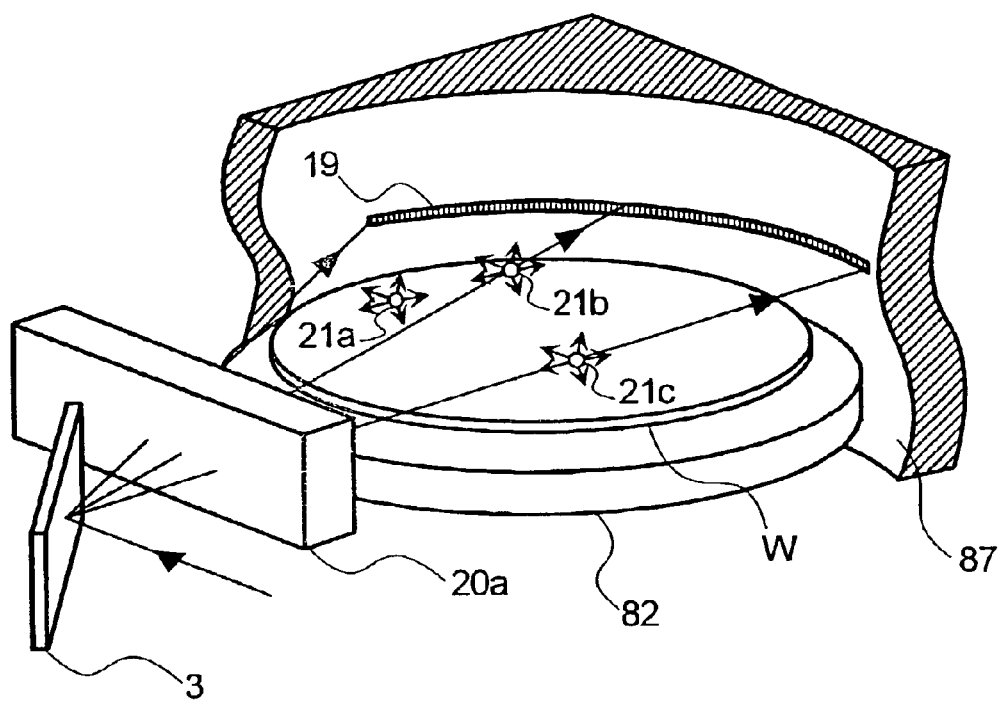
FIG. 2 is a diagrammatic view showing the illumination, foreign particles, foreign particle-scattered light, and the generation of scattered light by the inner walls of the processing chamber, relating to the present invention.

A method for detecting foreign particle-scattered light will be explained next. As shown in FIG. 2, the intensity modulated beam 102, that has been guided into the plasma processing chamber 86, is scattered by foreign particles 21a, 21b, 21c within the processing chamber. In the foreign particle-scattered light, mainly back-scattered light is detected by a detecting lens 22, having a detecting optical axis that is inclined with respect to the illuminating optical axis, in a plane parallel to the wafer surface through the viewing window 20a, as shown in FIG. 1(*b*) and FIG. 5(*a*). In this way, the detecting optical axis of the detecting lens 22 is different from the illuminating optical axis of the lens group 6, including the scanning optical system 3, and thereby it becomes possible to make it unnecessary to match up the detecting optical axis and illuminating optical axis. However, as the scanning optical system 3 is caused to scan, it is necessary that a beam, reflected rectangularly by the plane of incidence of the viewing, window 20a, is not incident to the pupil of the detecting lens 22. For this reason, the plane of incidence of the viewing window 20a may be slightly inclined with respect to the perpendicular direction.

Figure 3:
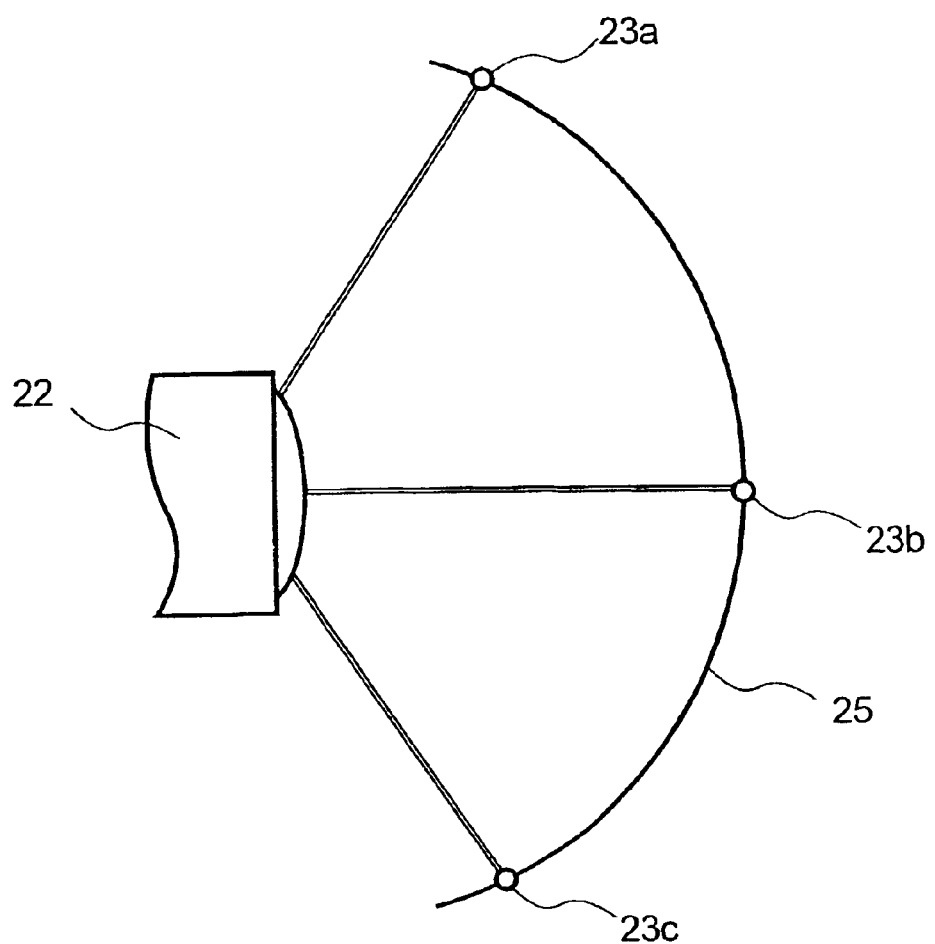
FIG. 3 is a diagram which illustrates an example of ray tracing for the detection of scattered light with the detecting lens.
Figure 4:
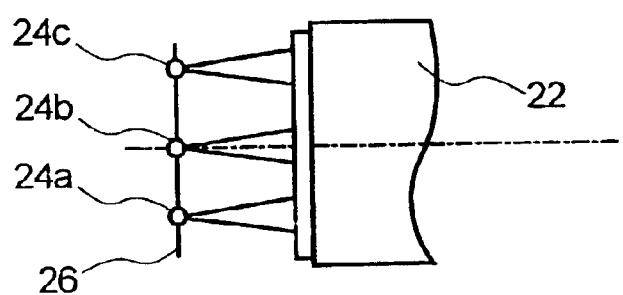
FIG. 4 is a diagram illustrating an example of ray tracing in the vicinity of the image plane of the detecting lens for foreign particle-scattered light detected by a detecting lens.
Figure 5:
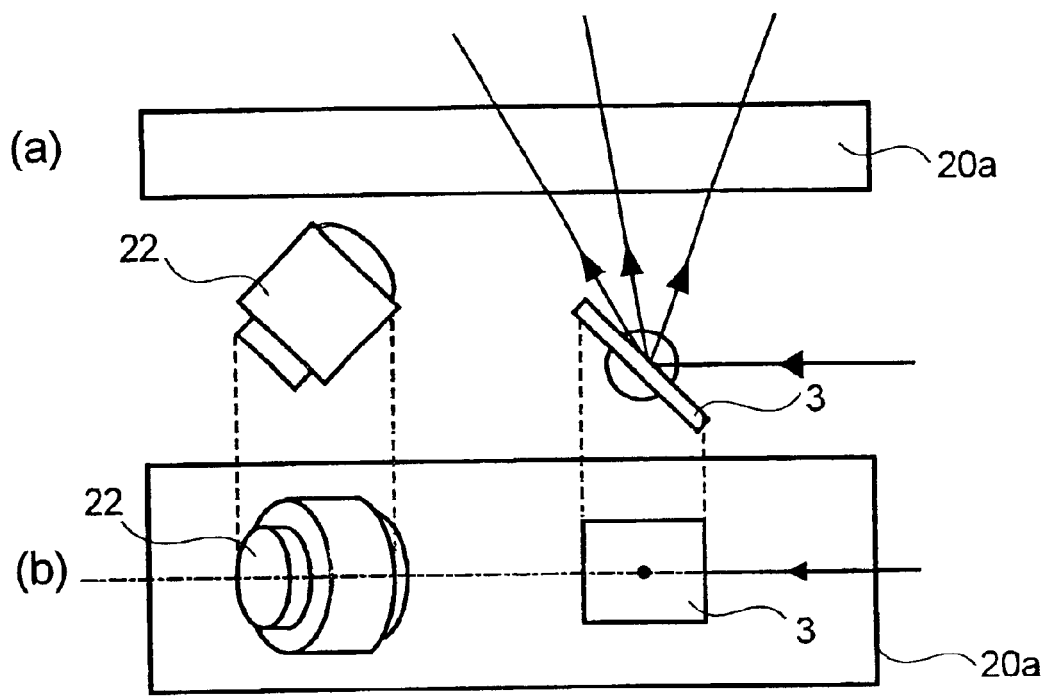
FIGS. 5(a) and 5(b) are side and top views, respectively, showing the physical relationship between the viewing window, scanning optical system, and detecting lens.

Because it is necessary to detect all of the back-scattered light from the floating foreign particles occurring in the entire plane above the substrate (wafer) W, the detecting lens 22 must be a lens having a wide field angle and/or a deep depth of field, such as a wide angle camera lens or a fish eye lens, as shown in FIG. 3. Specifically, the detecting lens 22 must image object points (floating foreign particles) 23a, 23b, 23c present in the object plane over the space (entire surface directly over the processed wafer substrate W), as shown in FIG. 3, at least in the plane parallel to the wafer surface, at image points 24a, 24b, 24c, respectively, on the image plane 26 of the detecting lens 22 (detection area limiting filter (spatial filter) 2).

As an example, the above-mentioned detecting lens 22 is a lens having a deep depth of field, such that the focal point matches the object point present at a location more distant than the minimum imaging distance. All of the foreign particle-scattered light occurring at locations farther than the above-mentioned minimum imaging distance is imaged at the image plane 26 of the detecting lens 22. In this case, in order to focus the foreign particle-scattered light occurring over the wafer W, the detecting lens 22 must be a lens having a minimum, imaging distance that is shorter than the distance from the detecting lens 22 to the closest point on the wafer W, having a depth of field longer than the wafer size in order to focus all of the foreign particle-scattered light occurring over the wafer W with uniform sensitivity regardless of the location where the scattered light occurs, and, furthermore, having a wide field angle in order to detect all of the foreign particle-scattered light occurring over the wafer W.

Figure 22:
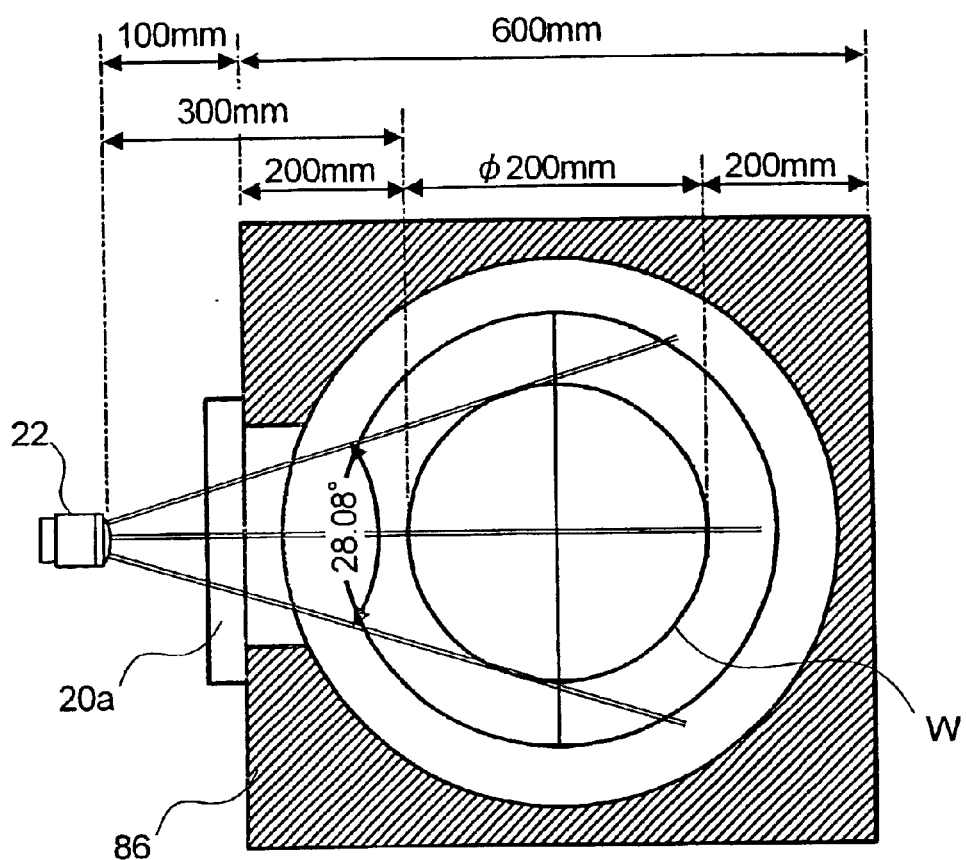
FIG. 22 is a diagrammatic cross-sectional view of the detecting lens and plasma processing chamber.

For example, as shown in FIG. 22, when the external dimensions of the plasma processing chamber 86 are 600 mm, the wafer W has a diameter of 200 mm, and the distance between the detecting lens 22 and the plasma processing chamber 86 is 100 mm, then the distance between the lens 22 and the nearest point on the wafer W becomes 300 mm, and the necessary minimum imaging distance becomes 300 mm or less. Also, the necessary depth of field must be 200 mm or greater, which corresponds to the diameter of the above-mentioned wafer, in order to focus all of the foreign particle-scattered light occurring over the wafer W with uniform sensitivity, regardless of the point at which the foreign particle-scattered light occurs. Also, the field angle necessary to detect all of the foreign particle-scattered light occurring over the wafer W becomes 28.08°. A lens which satisfies these requirements is, for example, the AF Fisheye Nikkor 16 mm F 2.8 D from Nikon. The minimum imaging distance of this lens is 250 mm, the depth of field ranges from infinity to the minimum imaging distance (for object points farther than the minimum imaging distance of 250 mm, all focus fits and the images are not blurred), and the field angle is 180°. Consequently, all of the foreign particle-scattered light occurring in the space over the wafer W can be detected at the same sensitivity with the detecting lens 22.

The foreign particle-scattered light detected with the detecting lens 22 is focused on the plane of incidence of the optical fiber 13. The end plane of incidence of this optical fiber 13 (light collecting area) may be of the same size or larger than the image plane of the detecting lens 22. For example, in the case of the above-mentioned AF Fisheye Nikkor 16 mm F 2.8 D from Nikon, the image size is a standard screen size of 24 by 36 mm of one frame of 35 mm film, and, therefore, the end plane of incidence of the optical fiber 13 (light collecting area) may be 24 by 36 mm or greater. The size of the end plane of incidence (light collecting area) of the optical fiber 13 that is actually necessary may be the region in which the foreign particle-scattered light occurs, in effect, the image size corresponding to the area illuminated by the intensity modulated beam 102 in the space over the wafer W. It is therefore possible to decrease the size of the end plane of incidence (light collecting area) of the optical fiber 13 as necessary. In order to ensure a large light collecting surface, methods using a bundled fiber or a liquid light guide as the optical fiber 13 are effective.

In the case where the outline of the processed substrate W is D and the distance between the detecting lens 22 and the center of the processed substrate W is L, the detecting lens 22 is provided as a lens having a deep depth of field such that the focal point matches the object points present at locations farther than the minimum imaging distance (L-(D/2)->, which is in the vicinity of the left end directly over the substrate W. All of the foreign particle-scattered light occurring at locations farther than the above-mentioned minimum imaging distance (entire region from near the left to near the right end over the substrate W) is imaged in the image plane 26 of the detecting lens 22. Moreover, if the size of the plane of incidence (light collecting area) of the optical fiber 13 is greater than the size of the image plane of the detecting lens 22, then the detecting lens 22 does not necessarily need to be constituted with a lens having a deep depth of field. After all, the detecting lens 22 needs to be able to cause the back-scattered light, received from floating foreign particles occurring over the entire surface of the substrate (wafer) W, to strike the plane of incidence of the optical fiber 13. For this reason, the detecting lens 22 is minimally constituted, having a wide field angle, as shown in FIG. 3.

Consequently, the detecting lens 22 can cause the back-scattered light received from the floating foreign particles occurring over the entire surface of the substrate (wafer) W, to strike the plane of incidence of the optical fiber 13 and to detect, with uniform sensitivity, the foreign particle-scattered light occurring in a wide space within the processing chamber 86. Of course, the detecting lens 22 may also be able to image all of the back-scattered light from floating foreign particles occurring over the entire surface of the substrate (wafer) W at the image plane (spatial filter 2) 26. In this case, as will be explained in detail below, with just a small difference in height between the detecting optical axis and the illuminating optical axis, it becomes possible to block scattered light reflected from the walls using the spatial filter 2.

In the case where the diameter of the substrate W is D and the distance between the detecting lens 22 and the center of the substrate W is L, it is necessary that the wide field angle (apparent angle) 20 of the detecting lens 22 be tan θ>((D+α)/2)/L. In the case where the diameter of the substrate is 8 to 12 inches, D becomes 203 to 304 mm, and therefore (D+α) is 300 to 400 mm or greater, and L must become 500 to 750 mm or greater. As a result, the wide field angle (apparent angle) 2θ of the detecting lens 22 must become 30 to 34° or greater. When the apparent angle of the detecting lens 22 is 2θ, and when the field number of the detecting lens 22 is FA, the focal distance is f, and the magnification is m, the relationship in the following equation (1) is developed.

$$\tan\theta = (FA/2) \cdot (1/f) = FA \cdot (m/500) \qquad (1)$$

As explained above, the foreign particle-scattered light detected by the detecting lens 22 is focused on the plane of incidence of the optical fiber 13. Moreover, the plane of incidence of the optical fiber 13 (light collecting area) is of the same size or greater than the image plane of the detecting lens 22. Consequently, the optical fiber 13 is able to detect, with uniform sensitivity, the foreign particle-scattered light occurring in a wide space within the processing chamber 86. In this way, methods using a bundled fiber or liquid light guide are effective in order to ensure a large light collecting surface (plane of incidence).

Moreover, the vertical disposition perpendicular to the wafer surface of the detecting lens 22 may be at the same height as the galvanomirror (scanning optical system) 3, as shown in FIG. 5(b). In this case, an effort must be made so that reaction products do not accumulate on the inner walls 87 of the processing chamber 86, for transparency, for example, so that scattered light 19 from the laser beam illumination reflected therefrom does not occur, and for reflection, for example, so that the light 19 does not strike the detecting lens 22.

Figure 6:
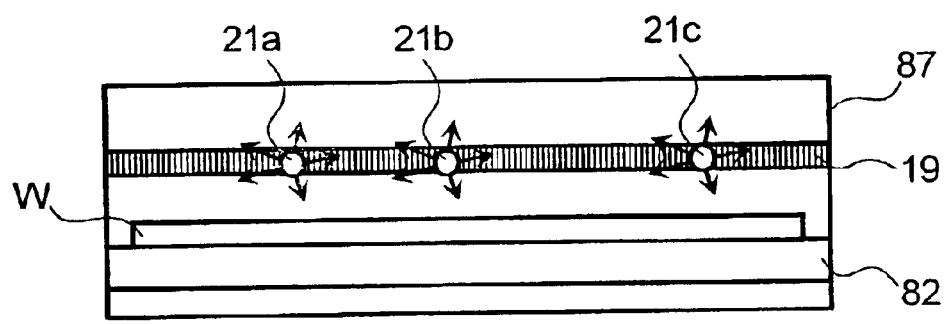
FIG. 6 is a diagram illustrating an image in the image plane of the detecting lens relating to the first embodiment of the present invention.

Normally, however, in relation to the reaction products accumulating on the inner walls 87 of the processing chamber 86, high intensity scattered light is reflected from the inner walls when the laser beam illuminates the inner walls. As a result, when the height of the detecting optical axis of the detecting lens 22 is the same as the height of the illuminating optical axis, such that the laser beam 102 is reflected by the galvanomirror 3 and illuminates the inside of the processing chamber 86, as shown in FIG. 6, the back-scattered light from foreign particles and the high intensity scattered light 19 reflected from the inner walls of the processing chamber pass through the viewing window 20a, strike the detecting lens 22, and are imaged at positions of the same height in the image plane 26 of the detecting lens 22. Therefore, the reflected light, which cannot be blocked using the spatial filter 2 and strikes the optical fiber 13, cannot be eliminated from subsequent processing, and, therefore, it becomes a major background noise.

Figure 7:
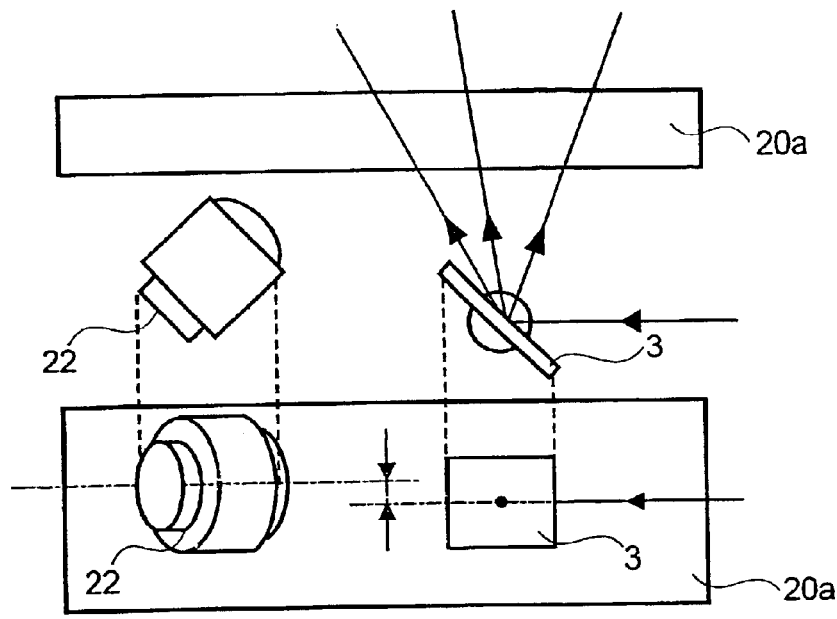
FIG. 7 are side and top views, respectively, showing the physical relationship between the viewing window, scanning optical system, and detecting lens according to the first embodiment of the present invention.
Figure 8:
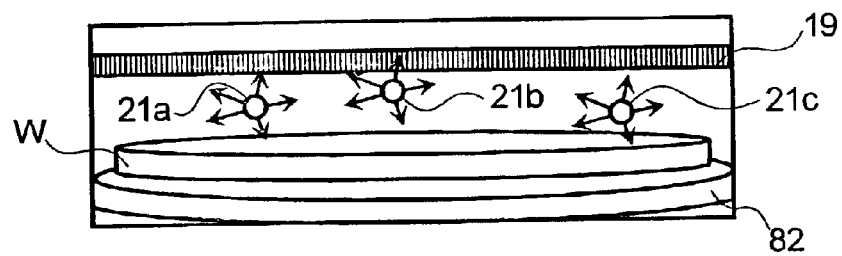
FIG. 8 is a diagram illustrating an image in the image plane of the detecting lens relating to the first embodiment of the present invention.
Figure 9:
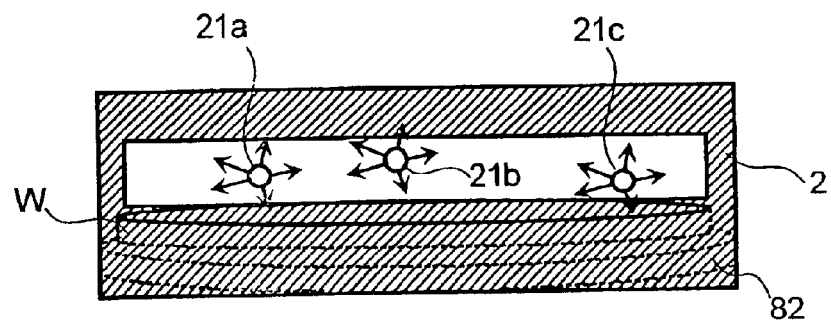
FIG. 9 is a diagram illustrating the detected image when a detection area limiting filter (spatial filter) is present, in the first embodiment of the present invention.

As shown in FIG. 7, with respect to the direction perpendicular to the wafer surface, the detecting optical axis of the detecting lens 22 has a height different from that of the illuminating optical axis of the galvanomirror (scanning optical system) 3. In the case where the detecting optical axis is disposed at a high position, as shown in FIG. 8, for example, the back-scattered light from foreign particles and the scattered light 19 reflected from the inner walls 87 of the processing chamber are imaged at different heights in the image plane 26 of the detecting lens 22. Consequently, as shown in FIG. 9, the detection area limiting filter (spatial filter) 2 blocks the area outside the region where the foreign particle-scattered light to be detected is imaged. The scattered light 19 reflected from the inner walls 87 of the processing chamber is thereby made undetectable. Moreover, when the detecting lens 22 is a lens having a deep depth of field, the back-scattered light from foreign particles and the scattered light 19 reflected from the inner walls 87 of the processing chamber are imaged with certainty at positions of different heights in the image plane 26 of the detecting lens 22. Therefore, it becomes unnecessary to make the height of the detecting optical axis greatly different from the height of the illuminating optical axis.

Furthermore, as noted in Japanese Patent Laid-open Publication No. 1111-251252, the output end of the optical fiber 13 is connected to a splitter 14, such as a monochrometer or interference filter, set to the wavelength of the laser beam 101 output from the laser beam source 9. After effecting wavelength division of only the foreign particle-scattered light wavelength component from the plasma emission, the light undergoes photoelectric conversion with a photoelectric converting element (photodetector) 15, such as a photoelectric multiplier tube. The detection, signal which underwent photoelectric conversion is amplified using an amplifying circuit 16, and it then undergoes synchronous detection with a lock-in amp (synchronous detection circuit), with the reference signal being a rectangular signal, having a frequency of 170 kHz and duty of 50%, output from the oscillator 11 that is used in the intensity modulation of the laser beam. The foreign particle-scattered light component with a frequency of 170 kHz is then extracted from the above-mentioned detection signal.

Through experiment, the inventors have verified the intensity of the plasma emission being synchronized with the modulation frequency of the highway frequency power for plasma excitation. For example, the foreign particle signal undergoes' wavelength separation by the splitter 14 from the emission of plasma generated by the high frequency power at the plasma excitation frequency of 400 kHz, as mentioned above, and then modulation and synchronous detection thereof at the plasma excitation frequency and the frequency of 170 kHz, which is different from an integral multiple thereof. This foreign particle signal is divided by two wavelength and frequency areas from the plasma emission and is detected. With this method, the inventors confirmed by experiment that it was possible to detect, with good sensitivity weak foreign particle-scattered light from the plasma emission.

Figure 10:
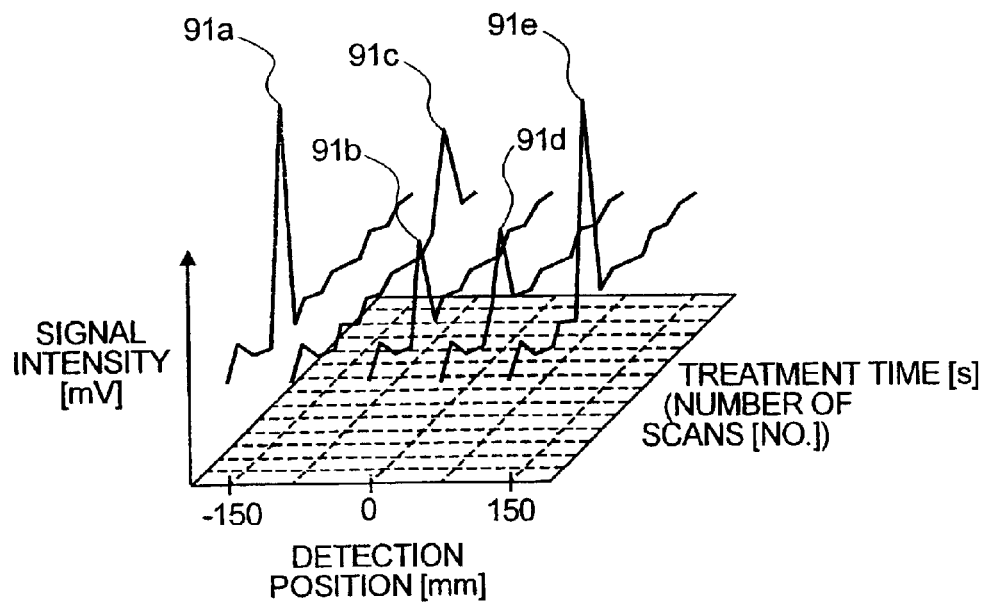
FIG. 10 is a three-dimensional graph which shows the change over time of the detected light intensity at nine points on the processed substrate (wafer) in the first embodiment of the present invention.
Figure 11:
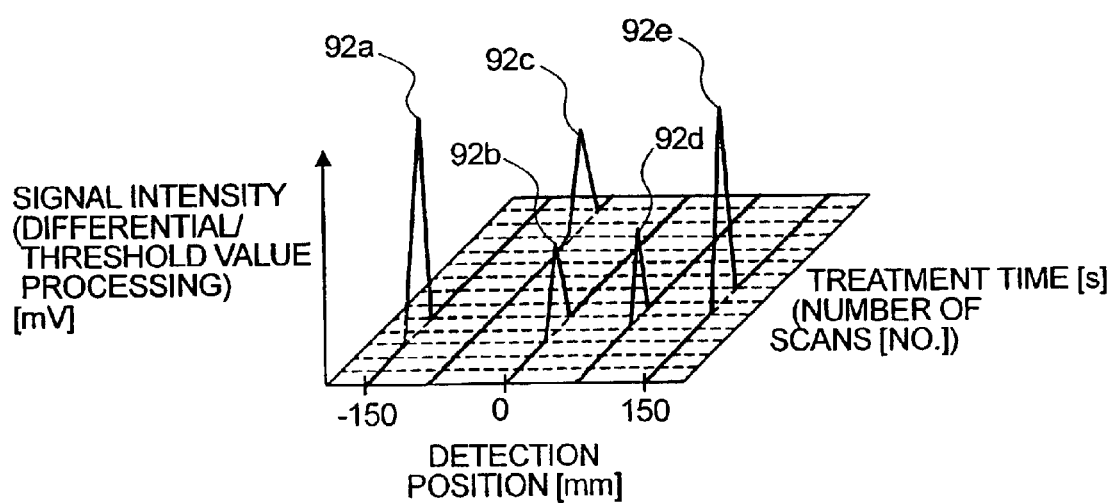
FIG. 11 is a three-dimensional graph which shows the foreign particle signal intensity at nine points on the processed substrate (wafer) in the first embodiment of the present invention.

The output of the lock-in amp (synchronous detection circuit) 17 is sent to the computer 18. In the computer 18, the scanning signal is sent through the scanning optical system driver 4 to the galvanomirror (scanning optical system) 3, and the beam is scanned. Meanwhile, the foreign particle signals 91a to 91e, which are taken up at each scanning position, are displayed on a detailed display 7 in the form as shown in FIG. 10, for example. As shown in FIG. 11, at each detection position, that difference between the output at the n-th scanning time and the output at the (n−1) scanning time is found, and signals 92a to 92e are shown only when the change is greater than a given value, whereupon the determination of the foreign particle signal becomes easy.

In connection with the above-mentioned embodiment, coordinates are taken on the diameter of 300 mm (corresponds to a 12 inch wafer), the coordinates being on the horizontal axis, and calculation results for five illumination beams on the wafer are displayed on the basis of such coordinates. In the case of light scattered by foreign particles in the processing chamber 86, large pulse signals 92a, 92b, 92c, 92d, and 92e appear for five locations, as seen in FIG. 11. In the computer 33, the signal intensity with respect to grain diameter, attained in advance by experiment, and the detected foreign particle signal intensity are compared, and the following facts are determined: the size of the foreign particles, the number of foreign particles from the number of the above-mentioned large pulse signals, and the location of the foreign particles from the scanning position when the signal was detected. Furthermore, in the computer 18, the state of contamination of the processing chamber is determined from the number and size of foreign particles detected. When the total number of foreign particles exceeds a predetermined standard value, a signal is sent to the etching process apparatus controller 88, and the etching process is ended, and information to inform the operator of the etching process apparatus of the state of contamination is output using an alarm or a light.

As explained above, with the present embodiment, it becomes unnecessary to match the illuminating optical axis and the detecting optical axis, because the illuminating optical axis of the laser beam having the scanning optical system 3 is made different from the detecting optical axis of the detecting lens 22. Moreover, by constituting the detecting lens 22 as a lens having a wide field of view (wide apparent angle), it becomes possible to separate the floating foreign particles from the plasma emission and detect these floating foreign particles, occurring over the entire region of a substrate, with uniform sensitivity in a plasma processing apparatus.

Furthermore, by making the height of the detecting optical axis of the detecting lens 22 different from the height of the illuminating optical axis of the laser beam having the scanning optical system 3 and blocking the scattered light reflected from the inner walls of the processing chamber using a spatial filter (detection area limiting filter), it becomes possible to separate the floating foreign particles from the plasma emission and detect floating foreign particles occurring over the entire region of a substrate in a plasma processing apparatus, without influence from scattered light reflected by the inner walls of the processing chamber, which becomes a source of major noise.

Figure 12:
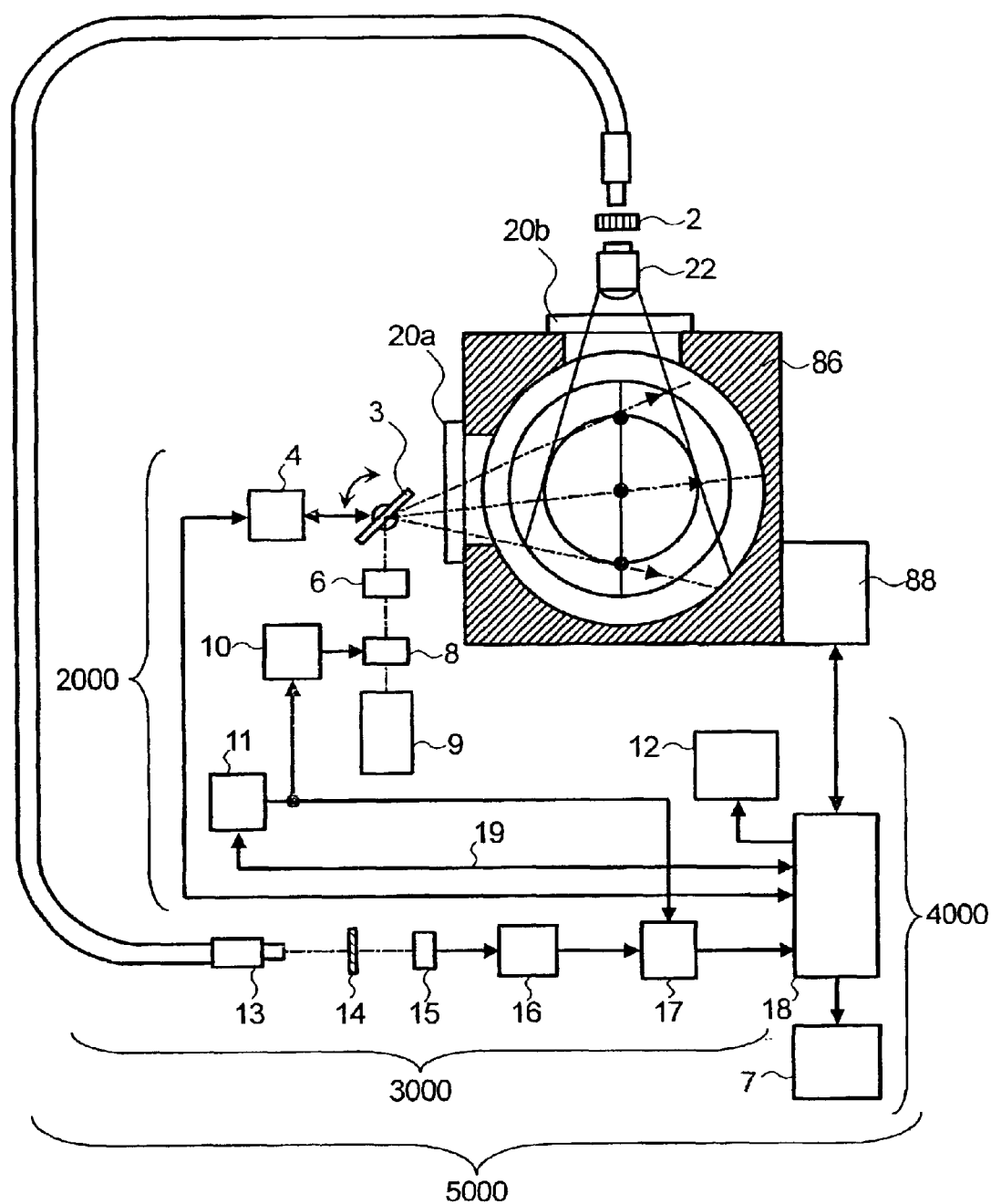
FIG. 12 is a schematic diagram showing a second embodiment of a plasma processing apparatus according to the present invention (an etching process apparatus having a device for measuring floating particles in the plasma)
Figure 13:
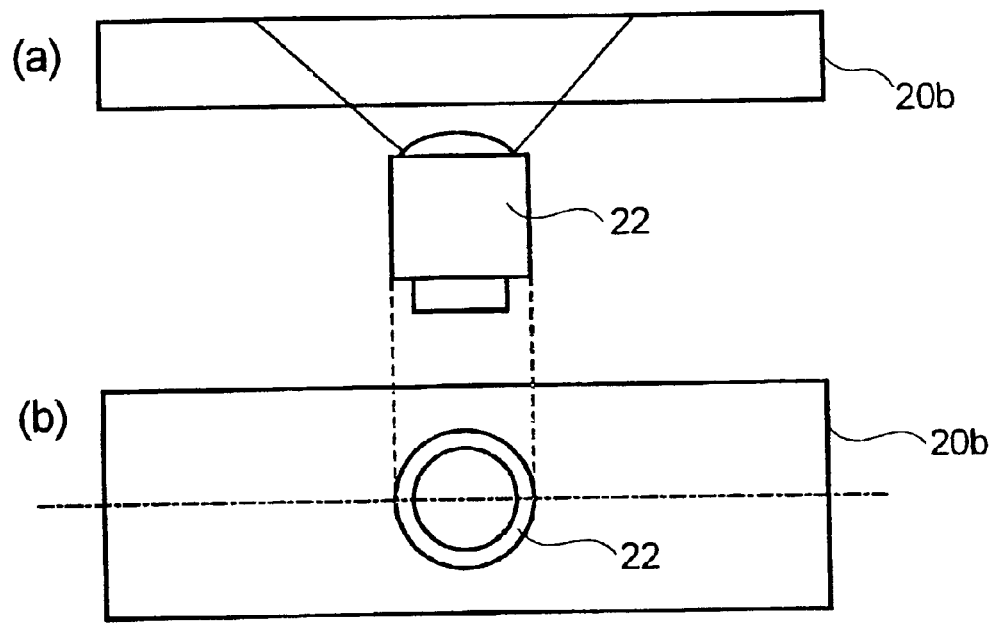
FIGS. 13(a) and 13(b) are side and top views, respectively, showing an image in the image plane of the detecting lens relating to the second embodiment of the present invention.

The second embodiment of the plasma processing apparatus relating to the present invention will be described next with reference to FIGS. 12 through 19. FIG. 12 is a schematic diagram showing the constitution of an etching process apparatus having a foreign particle monitor for the processing chamber, representing a second embodiment of the present invention.

In the second embodiment, aspects which are different from the first embodiment include the provision of an additional viewing window (window glass) 20b in the side wall of the plasma processing chamber 86 and the detection through the viewing window 20b of side-scattered light resulting from floating foreign particles by the detecting lens 22.

Figure 14:
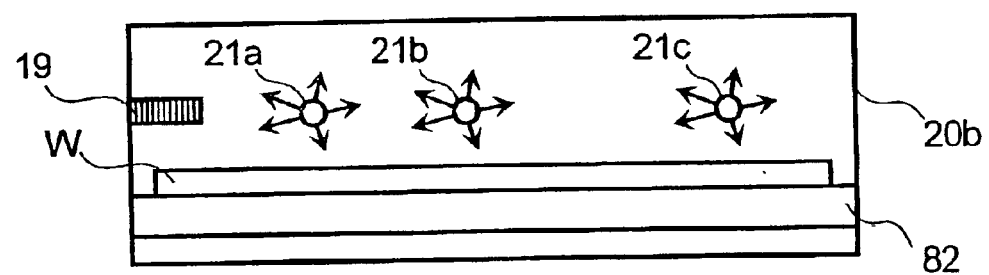
FIG. 14 is a diagram illustrating the physical relationship between the viewing window, scanning optical system, and detecting lens in the second embodiment of the present invention.
Figure 15:
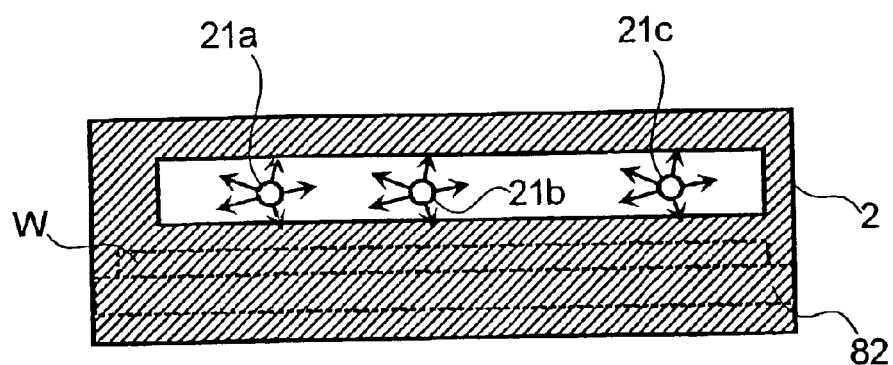
FIG. 15 is a diagram showing the detected image, when a detection area limiting filter (spatial filter) is present, in the second embodiment of the present invention.
Figure 16:
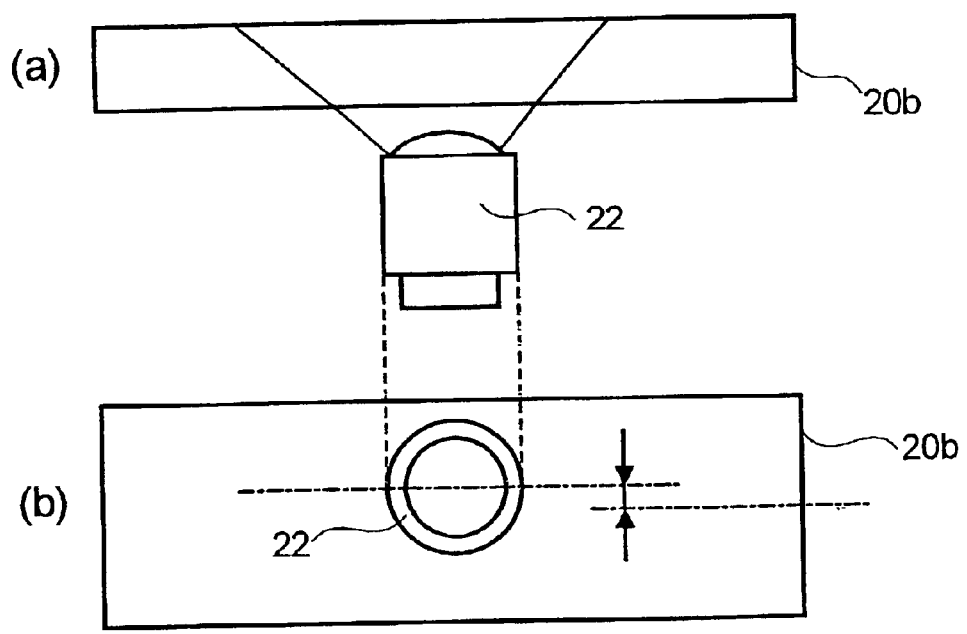
FIGS. 16(a) and 16(b) are side and top views, respectively, showing the physical relationship between the viewing window, scanning optical system, and detecting lens in the second embodiment of the present invention.

FIG. 13(b) shows the case where the height of the optical axis for detection by the detecting lens 22 is matched with the height of the optical axis for illumination by the laser beam having the scanning optical system 3. In this way, in the case of the second embodiment, the scattered light 19 reflected from the walls of the processing chamber only slightly impinges on the detecting lens 22, as shown in FIG. 14. Therefore, as shown in FIG. 15, it becomes possible to block the scattered light 19 with a spatial filter (detection area limiting filter) 2. Also, even if the computer 18 cancels the output of the lock-in amp (synchronous detecting circuit) 17 based on the scanning signal to the scanning optical system 3 through the driver 4, and even if the scattered light 19 reflected from the walls of the processing chamber only slightly impinges on the detecting lens 22 as shown in FIG. 14, it becomes possible to eliminate the influence thereof.

Figure 17:
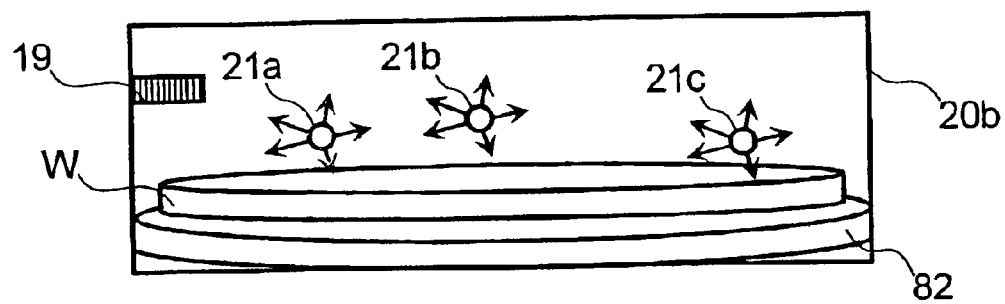
FIG. 17 is a diagram showing an image in the image plane of the detecting lens in the second embodiment of the present invention.
Figure 18:
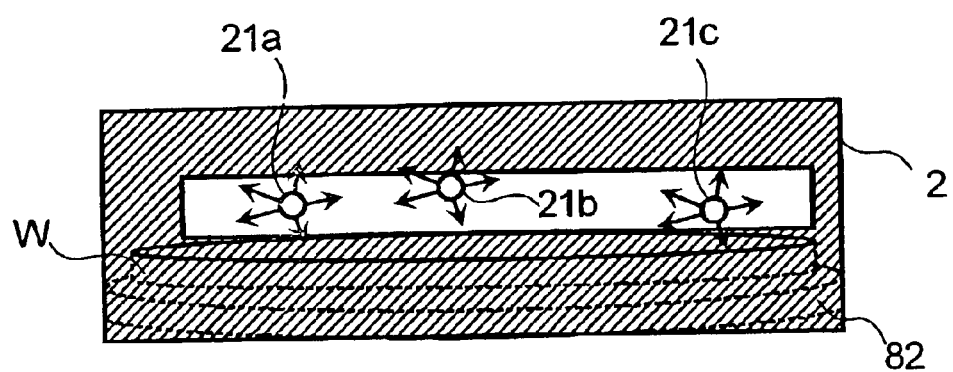
FIG. 18 is a diagram showing the detected image, when a detection area limiting filter (spatial filter) is present, in the second embodiment of the present invention.

Of course, as shown in FIG. 16(b), it is also possible in this embodiment to make the height of the optical axis for detection by the detecting lens 22 different from the height of the optical axis for illumination by the laser beam having the scanning optical system 3. In this case, the scattered light 19 reflected from the walls of the processing chamber impinges only slightly on the detecting lens 22, as shown in FIG. 17; therefore, the scattered light 19 can certainly be blocked by the spatial filter 2, as shown in FIG. 18.

As explained above, even in the second embodiment, as in the first embodiment, it becomes unnecessary to match the illuminating optical axis and the detecting optical axis because the illuminating optical axis of the laser beam having the scanning optical system 3 is made different from the detecting optical axis of the detecting lens 22. Moreover, by using a detecting lens 22 with a wide field of view (wide apparent angle), it becomes possible to separate the floating foreign particles from the plasma emission and detect these floating foreign particles, occurring over a wide space across the entire region of a substrate, with uniform sensitivity in a plasma processing apparatus.

A third embodiment of the plasma processing apparatus relating to the present invention will be described. In this third embodiment, aspects which are different from the first embodiment include the establishment of an additional viewing window (window glass) at a position opposite to the viewing window 20a in the plasma processing chamber 86, and the detection through that viewing window of forward-scattered light resulting from floating foreign particles over the substrate W by the detecting lens 22. In the third embodiment, as in the first and second embodiments, it becomes unnecessary to match the illuminating optical axis, and detecting optical axis because the illuminating optical axis of the laser beam having the scanning optical system 3 is made different from the detecting optical axis of the detecting lens 22. Moreover, by using a detecting lens 22 with a wide field of view (wide apparent angle), it becomes possible to separate the floating foreign particles from the plasma emission and detect such floating foreign particles, occurring over a wide space across the entire region of a substrate, with uniform sensitivity in a plasma processing apparatus.

Moreover, in the case of the third embodiment, it is necessary that the illuminating laser beam go straight into the plasma processing chamber. Also, forming the viewing window identically to the detecting area limiting filter, or establishing a limiting filter is necessary so that the straight-traveling illuminating laser beam does not impinge on the detecting lens 22. However, the illuminating laser beam 102 is caused to strike the viewing window 20a, while being scanned with the scanning optical system 3. Furthermore, in relation to the reaction products adhering on the inside of the viewing window 20a, the illuminating laser beam may be scattered and not travel straight through the plasma processing chamber. For this reason, the intensity of forward-scattered light caused by floating foreign particles is high compared to side-scattered light and back-scattered light; however, because it is difficult to keep the illuminating laser beam from striking the detecting lens 22, the first and second embodiments are superior.

As explained above, with the first through third embodiments, it is not necessary to match the illuminating optical axis and detecting optical axis, and, moreover, the detecting lens 22 is constituted with a wide field of view (wide apparent angle), and the system includes a modulation and synchronous detection system. As a result, it becomes possible to separate the floating foreign particles from the plasma emission and detect weak foreign particle-scattered light in two wavelength and frequency areas. This weak scattered light is a problem when detecting foreign particles in plasma with a simplified detecting optical system. Also, the minimum detection sensitivity attained with only conventional wavelength separation is limited to about 1 $\mu$m diameter particles, but the minimum detection sensitivity can be greatly improved to 0.2 $\mu$m diameter particles. Another effect is that it becomes possible to detect foreign particles with stability across the entire wafer surface, and, at the same time, it is possible to monitor the state of contamination of the inner walls of a plasma processing chamber.

Also, with the first through third embodiments, foreign particle detection is effected across the entire surface of the processed substrate and the number, size, and distribution of foreign particles are determined. As a result, the operator can confirm this information in real time on a display, for example.

Also, with the first through third embodiments, the state of contamination within a plasma processing chamber can be determined in real time, and, at the same time, the state of contamination of the inner walls of the processing chamber can be monitored, based on the information attained regarding the number, size, and distribution of foreign particles. As a result, it is possible to improve the availability factor of the apparatus by optimizing the cleaning time, thereby to make possible early discovery of the sudden occurrence of a large quantity of foreign particles, and to improve the yield. Also, because the process continues while the state of contamination in the plasma processing chamber is continually monitored, the semiconductor substrates and liquid crystal substrates processed in this way become high-quality, highly reliable products which have been processed in an environment that does not include foreign particles beyond a reference value.

Also, with the first through third embodiments, it becomes possible to reduce the frequency of carrying out processing to determine the state of contamination of the processing chamber using a dummy wafer, and of determining the state of contamination using sampling inspections; and, therefore, dummy wafer costs are reduced.

Figure 19:
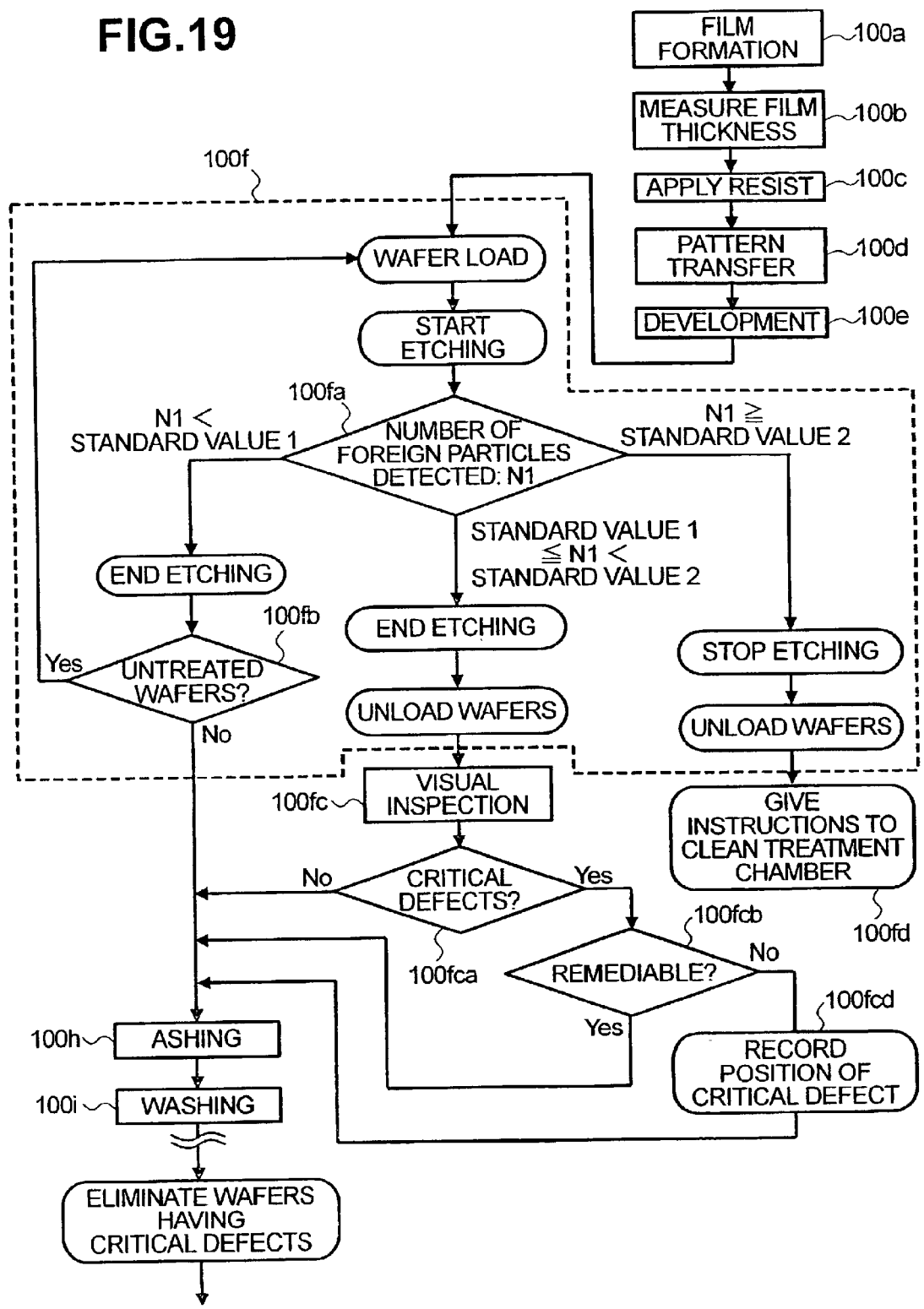
FIG. 19 is a process flow diagram showing the typical process flow, for the steps in the processing of a semiconductor integrated circuit device, using a plasma processing apparatus with a device for measuring floating foreign particles in a plasma, according to the present invention.
Figure 20:
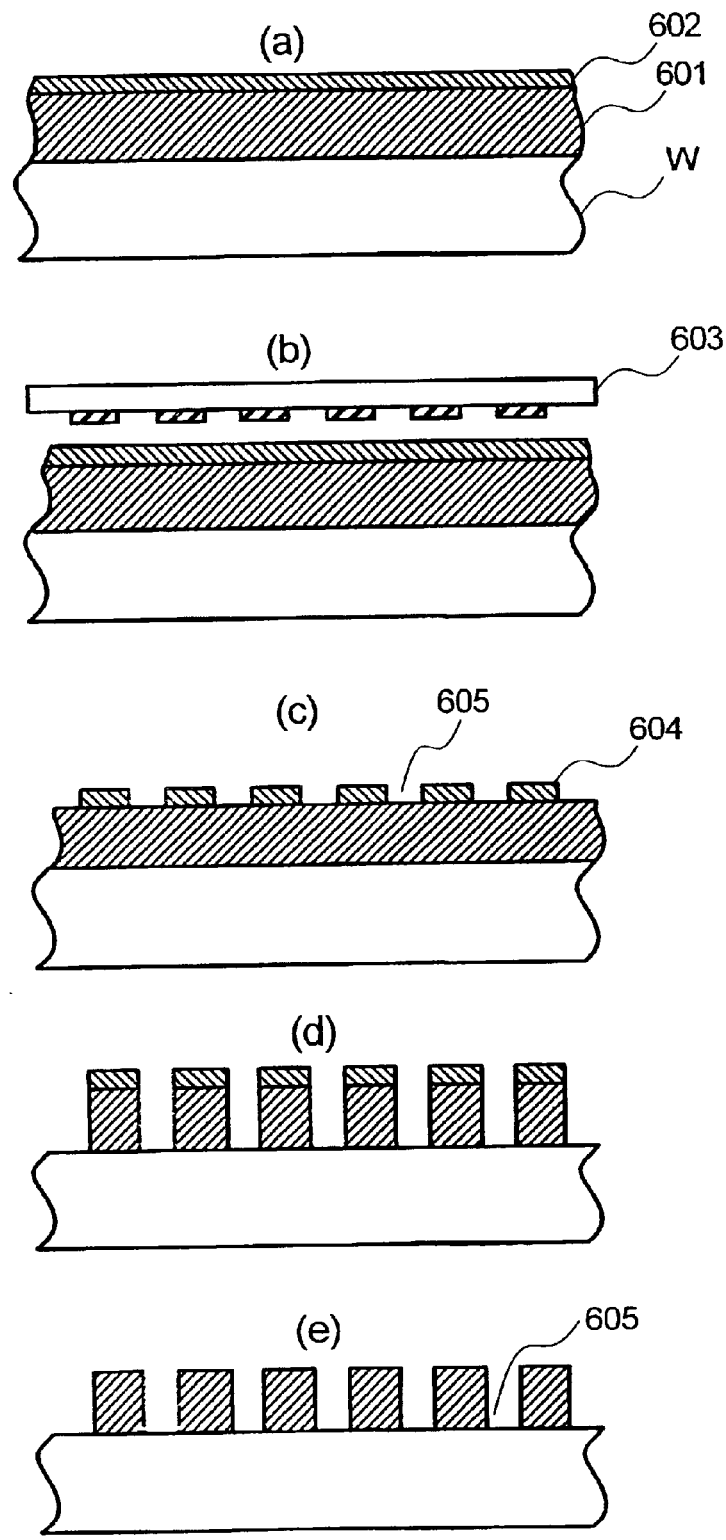
FIGS. 20(a) to 20(e) are diagrams illustrated the typical process flow using cross sectional structures to show the process for forming a contact hole, according to the present invention.
Figure 21:
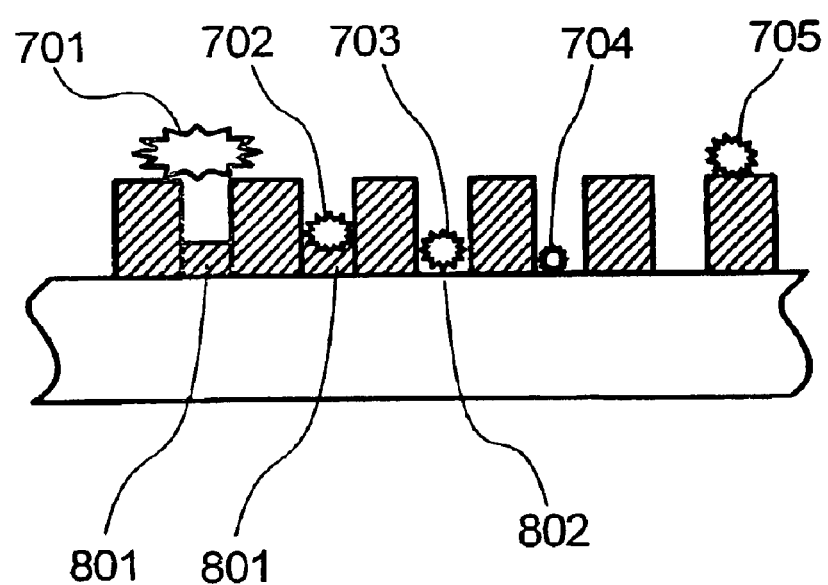
FIG. 21 is a diagram showing a typical example of a defect occurring because of adhered particles in the process of etching a contact hole.

Next, an embodiment of the semiconductor processing method using the floating foreign particle monitoring technology in a plasma processing apparatus relating to the present invention will be explained with reference to FIGS. 19, 20, and 21.

Referring to FIGS. 19 and 20(a) to 20(e), an outline of the processing method for use in a semiconductor integrated circuit apparatus relating to the present invention will be explained.

As shown in FIG. 20(a), the process 100a is a film growth process for forming a processed film 601, such as a silicon dioxide film, on a wafer W. The process 100b is a film thickness measuring process for inspecting the thickness of the film being formed. As shown in FIG. 20(a), the process 100c is a resist application process for applying a resist 602 on the wafer W. As shown in FIG. 20(b), the process 100d is a pattern transfer process for transferring a mask pattern 603 onto the wafer. As shown in FIG. 20(c), the process 100e is a developing process for removing the processed portions of the resist 605. As shown in FIG. 20(d), the process 100f is an etching process, wherein the resist pattern 604 is the mask, the processed film 601 of the resister removal portion 605 is etched, and wiring trenches and contact holes 606 are formed. As shown in FIG. 20(e), the process 100h is an ashing process to remove the resist pattern 604. The process 100i is a washing process which is used to wash the wafer surface and back surface. The above-mentioned series of processes is carried out for the formation of contact holes, for example.

Defects resulting from foreign particles occurring during etching and adhering to the wafer will be explained next with reference to FIG. 21. FIG. 21 is a diagram showing an example of a defect occurring during contact hole etching, for example.

The foreign particle 701 represents a particle that has adhered to the contact hole opening during the etching process. In this case, because the etching reaction is stopped by the adhered particle, the contact hole at the section where the particle is adhered is not opened, so that the presence of the foreign particle 701 becomes a critical defect.

The foreign particle 702 represents a particle that has adhered to the inside of the contact hole during etching. In this case as well, because the etching reaction is stopped by the adhered particle, the contact hole at the section where the particle is adhered is not opened, so that the presence of the foreign particle 701 becomes a critical defect.

The foreign particles 703 and 704 represent particles that have adhered to the inside of the contact holes after etching is completed. Particles adhered at locations with a high aspect ratio, such as contact holes, are often difficult to remove even during the washing process, and, in the case of large particles, such as the particle 703, these become critical defects because contact is no good.

The foreign particle 705 represents a particle that has adhered on the resist pattern 604 during the etching process. In this case, the etching reaction is not influenced by the adhered particle 705 and a critical defect does not result from the adhered particle 705.

In this way, critical defects do not occur in the case where the size of the particle is not large enough to cause a defect, or in the case where the location of adherence is in an area that is not etched; thus, all particles that have adhered to the wafer do not cause critical defects. Also, while foreign particles 701 and 705 are particles that are relatively easily removed by washing, particles that have dropped into contact holes with a high aspect ratio, such as particles 602, 703, and 704, are difficult to remove by washing.

In accordance with the present invention, in the etching process 100f, where the etching process apparatus 80 is employed, foreign particles generated in the processing chamber during etching is detected in real time by the measurement apparatus 5000 for floating particles in plasma. In the foreign particle determination process 100fa, the computer 18, or the controller connected to the computer 18, selects an action from among the following based on the foreign particle detection results: to send the processed wafer to the next process and to continue the process 100f for the remaining wafers; to perform a visual inspection 100fc, before sending the wafer to the next process; or to stop the process and performed cleaning (maintenance) 100fd of the processing chamber.

The process to be performed next is selected by comparing the size and number of detected foreign particles with a predetermined standard value (foreign particle control standard).

An example of the method for calculating the above-mentioned standard value (foreign particle control standard) relating to the present embodiment will be explained next. As already explained, even if foreign particles are adhered on the wafer, all of the particles will not cause critical defects. The probability for critical defects resulting from adhered particles can be calculated from the relationship between the open area ratio and the pattern density of the etching pattern, as well as the line width, to the size and number of the foreign particles that have adhered to the wafer. Consequently, the correlation between the size and number of foreign particles detected during the etching process with the size and number of foreign particles that have adhered to the wafer is found in advance by experiment, and the probability for a critical defect to result from the foreign particles detected during etching can be, determined.

The standard value (foreign particle control standard) is established based on the value calculated using the above-mentioned method. An example of setting a standard value in the present embodiment is set forth below.

In the foreign particle determining portion 100fa, if the number Ni of detected foreign particles of a certain size or greater is less than a prescribed value 1, the standard value 1 is set, such that the probability of a critical defect occurring is very low (for example, the critical defect probability is 1% or less). For example, the standard value 1 is 10 particles with a diameter of 0.4 μm or greater.

In the foreign particle determining portion 100fa, if the number N1 of detected particles of a certain size or greater is greater than the above-mentioned prescribed value 1 and less than a prescribed value 2, the standard value 2 is set, so as to become a value where the occurrence of critical defects is a concern (for example, the critical defect probability is 5% or less). For example, the standard value 2 is 30 particles with a diameter of 0.4 μm or greater.

In the foreign particle determining portion 100fa, if the number N1 of detected particles of a certain size or greater is greater than the above-mentioned prescribed value 2, many critical defects will occur (for example, the critical defect probability is 5% or greater).

When the number N1 of particles of a certain size or greater that has been detected during etching process is less than the above-mentioned prescribed value 1, based on the above-mentioned prescribed value, the probability of a critical defect occurring is low, and, therefore, the next wafer process 100fb is performed.

When the number Ni of particles of a certain size or greater that has been detected during etching process is greater than or equal to the above-mentioned prescribed value 1, but is less than the above-mentioned prescribed value 2, a visual inspection 100fc will be performed after the etching process. If a critical defect is not confirmed in step 100fca as a result of the visual inspection, the wafer is sent on to the ashing process 100h. If a critical defect is confirmed in step 100fca as a result of the visual inspection, it is determined whether the critical defect is a remediable defect. When the defect is determined to be a remediable defect (by using a salvage circuit), based on the above-mentioned determination results, the wafer is sent on to the ashing process 100h. When it is determined that the defect is not a remediable defect, based on the above-mentioned determination results in step 100fcb, the wafer is sent on to the next ashing process 100h after the location of the defect is recorded in step 100fcd. Thereafter, the chip including the above-mentioned unremediable defect is thrown out when the chips are separated by dicing, for example.

When the number Ni of particles of a certain size or greater that has been detected during etching process is greater than the above-mentioned prescribed value 2, it is highly possible that a large number of critical defects will occur even on wafers which undergo processing thereafter. Therefore, the operator of the etching apparatus is informed by a display on a monitor screen, or by an alarm, to interrupt the etching process and perform cleaning (maintenance) 100fd inside the plasma processing chamber.

In an etching process apparatus which is not provided with an apparatus for measuring floating foreign particles in a plasma, the cleaning of the processing chamber may not necessarily be performed at the optimal time. Consequently, on the other hand, cleaning may be performed at a time when it is not necessary, and the utilization rate of the apparatus drops; or, on the other hand, the process continues as time passes when cleaning should be performed, so that a large quantity of bad items is produced, and the yield drops.

Also, there is a method wherein advance processing using a dummy wafer is performed to check the foreign particles in the processing chamber, and the cleaning time is determined from the results thereof. In this case, because excess work must be done for this series of processes, the throughput drops and the cost for the dummy wafer must be incurred. For larger wafer sizes, the increased cost of the dummy wafer is unavoidable, and a major issue is a reduction of advance work using dummy wafers to check foreign particles in the processing chamber.

On the other hand, with use of the present invention, because processing of the substrates can be performed at the same time as real-time monitoring of the state of contamination in the processing chamber, the cleaning time can be optimized. Because advance work using a dummy wafer is not necessary, the throughput can be improved and the dummy wafer costs can be reduced. Also, products processed with the processes of the present invention are products of good quality, which do not include foreign particles of greater than or equal to a prescribed value; and, consequently, products can be processed with a high reliability.

In the above-mentioned embodiments, examples of the application of the present invention to an etching process apparatus were discussed, but as noted before, the scope of the application of the present invention is not limited to this, and the present invention may be applied to ashing apparatuses or film growth apparatuses, for example. This makes it possible to achieve real-time monitoring of foreign particles in the ashing apparatuses and film growth apparatuses. It thereby becomes possible to reduce problems occurring in the ashing process and film growth process during the photolithography process, and it becomes possible to prevent the occurrence of defective products and improve the yield.

The present invention contributes to the effects of making possible a stable detection of foreign particles across the entire surface of a substrate, while greatly improving the detection sensitivity of foreign particles floating in a plasma, and simplifying the detecting optical system. At the same time, another effect is that it becomes possible to monitor the state of contamination of the walls of the plasma processing chamber.

Also, with the present invention, the state of contamination in a processing chamber can be determined in real time; and, at the same time, the state of contamination of the inner walls of the processing chamber can be monitored based on information attained on the number, size and distribution of foreign particles. As a result, the utilization rate of the apparatus is improved due to the optimization of the cleaning time, the sudden occurrence of large quantities of foreign particles can be detected quickly, and the yields are improved. Because the process is continued while the state of contamination in the processing chamber is being continually monitored, the semiconductor substrates and liquid crystal substrates processed in this way become high-quality, high reliability products processed in an environment which does not include foreign particles of greater than or equal to a standard value.

The invention may be embodied other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

What is claimed is:

1. A method for processing semiconductor devices comprising:

an introduction step of introducing a semiconductor substrate into a processing chamber;

a plasma generating step of generating plasma in said processing chamber;

a processing step of processing the semiconductor substrate by effecting a reaction of said semiconductor substrate with said generated plasma in said processing chamber;

a foreign particle detection step of detecting foreign particles floating in or near said generated plasma in said processing chamber; and a removal step of removing said manufactured semiconductor substrate from the processing chamber;

wherein said foreign particle detection step comprises:

an irradiation step of irradiating a laser beam inside said processing chamber through a window of said processing chamber, and scanning the laser beam in a plane substantially parallel to and above the semiconductor substrate which substantially covers an entire surface of the semiconductor substrate inside said processing chamber by using a scanning optical system;

a detecting step of detecting light that is scattered, as a result of the scanning of the laser beam, from foreign particles floating above the semiconductor substrate, using a detecting lens optical unit having a wide view lens, which views the plane above the semiconductor substrate and has a wide view angle substantially covering the area above the semiconductor substrate through the window and has an optical axis different from an optical axis of the scanning optical system, and a sensor which receives the scattered light through the wide view lens and outputs a first signal; and a step of attaining floating foreign particle information from said first signal.

2. A method for processing semiconductor devices according to claim 1, wherein the light scattered from floating foreign particles is back-scattered light and/or side-scattered light from floating foreign particles.

3. A method for processing semiconductor devices according to claim 1, wherein said detecting lens optical unit has a deep depth of field that can form an image, at said plane of incidence without defocusing, of scattered light from foreign particles within said processing chamber, occurring at any point between the detecting lens optical unit and the point at which foreign particle-scattered light occurs closest to said detecting lens optical unit within the region illuminated by said laser beam, and between the detecting lens optical unit and the point at which foreign particle-scattered light occurs farthest from said detecting lens optical unit, within the region illuminated by said laser beam within said processing chamber.

4. A method for processing semiconductor devices according to claim 1, wherein scattered light reflected from the walls of the processing chamber and brought to the plane of incidence by the detecting lens optical unit in said detecting step is blocked by a spatial filter.

5. A method for processing semiconductor devices according to claim 1, wherein, in said detecting step, the light focused on said plane of incidence is guided by an optic fiber to a detector.

6. A method for processing semiconductor devices according to claim 1, wherein, in said detecting step, the height of the plane, including the illuminating optical axis of said scanning optical system, is different from the height of the plane, including the detecting optical axis of said detecting lens optical unit.

7. A method for processing semiconductor devices comprising:

an introduction step of introducing a semiconductor substrate into a processing chamber;

a plasma generating step of generating plasma in said processing chamber;

a processing step of processing the semiconductor substrate by effecting a reaction of said semiconductor substrate with said generated plasma in said processing chamber;

a foreign particle detection step of detecting foreign particles floating in or near said generated plasma in said processing chamber; and a removal step of removing said processed semiconductor substrate from the processing chamber;

wherein said foreign particle detection step further comprises:

an irradiation step of irradiating a beam, that is intensity modulated by a prescribed frequency with an intensity modulator, through a window provided in said processing chamber, and causing the beam to scan in a plane substantially parallel to and above the semiconductor substrate which substantially covers an entire surface of the semiconductor substrate in said processing chamber with a scanning optical system;

a detecting step of detecting light that is scattered, as a result of the scanning of the laser beam, from foreign particles floating above the semiconductor substrate, using a detecting lens optical unit having a wide view lens, which views the plane above the semiconductor substrate and has a wide view angle substantially covering the area above the semiconductor substrate through the window and has an optical axis different from an optical axis of the scanning optical system, and a sensor which receives the scattered light through the wide view lens and outputs a first signal; and a step of attaining floating foreign particle information by extracting from said first signal a signal component having the same frequency as said light, which was intensity modulated with the prescribed frequency.

8. A method for processing semiconductor devices according to claim 7, wherein the light scattered from floating foreign particles is back-scattered light and/or side-scattered light from floating foreign particles.

9. A method for processing semiconductor devices according to claim 7, wherein, in said detecting step, said detecting lens optical unit has such a deep depth of field as to form an image, at said plane of incidence without defocusing, of the scattered light from foreign particles within said processing chamber, occurring at any point between the detecting lens optical unit and the point at which foreign particle-scattered light occurs closest to said detecting lens optical unit within the region illuminated by said laser beam, and between the detecting lens optical unit and the point at which foreign particle-scattered light occurs farthest from said detecting lens optical unit, within the region illuminated by said laser beam within said processing chamber.

10. A method for processing semiconductor devices according to claim 7, wherein scattered light reflected from the walls of the processing chamber and brought to the plane of incidence by the detecting lens optical unit in said detecting step is blocked by a spatial filter.

11. A method for processing semiconductor devices according to claim 7, wherein the light focused on said plane of incidence is guided by an optic fiber to a detector in said detecting step.

12. A method for processing semiconductor devices according to claim 7, wherein the height of the plane, including the illuminating optical axis of said scanning optical system, is different from the height of the plane, including the detecting optical axis of said detecting lens optical unit in said detecting step.

13. A method for processing semiconductor devices according to claim 7, wherein, in said detecting step, said intensity modulated light has a prescribed wavelength and is separated into a light component having said prescribed wavelength from the light focused on the plane of incidence, and the separated light component is received by a detector and converted to a first signal.

14. A method for processing semiconductor devices according to claim 7, wherein, in said detecting step, the prescribed frequency for said intensity modulation is different from the excitation frequency of said generated plasma, or the emission frequency and the frequency obtained by multiplying the same by an integer.

15. A method for processing semiconductor devices according to claim 7, wherein, said foreign particle detection step further comprises a step of analyzing the state of contamination within said processing chamber or in the area over said semiconductor substrate based on said floating foreign particle information.

16. A method for processing semiconductor devices according to claim 15, further comprising a step of controlling the cleaning of said processing chamber based on said analysis results of the state of contamination.

17. A plasma processing method comprising:

an introduction step of introducing a substrate into a processing chamber;

a plasma generating step of generating plasma in said processing chamber;

a process step of processing said substrate by effecting a reaction of said substrate with said generated plasma in said processing chamber;

a foreign particle detection step of detecting foreign particles floating in or near said generated plasma in said processing chamber; and a removal step of removing a processed substrate, which has undergone processing, from the processing chamber;

wherein said foreign particle detection step further comprises:

an irradiation step of irradiating a light beam an intensity of which is modulated with a prescribed frequency by an intensity modulator, inside said processing chamber through a window of the processing chamber, and scanning the laser beam in a plane substantially parallel to and above the substrate which substantially covers an entire surface of the substrate inside said processing chamber by using a scanning optical system;

a detecting step of detecting light that is scattered, as a result of the scanning of the laser beam, from foreign particles floating above the substrate, using a detecting Lens optical unit having a wide view lens, which views the plane above the substrate and has a wide view angle substantially covering the area above the substrate through the window and has an optical axis different from an optical axis of the scanning optical system, and a sensor which receives the scattered light through the wide view lens and outputs a first signal; and a step of attaining floating foreign particle information by extracting from said first signal a signal component having the same frequency as said light, which was intensity modulated with the prescribed frequency.

18. A plasma processing method according to claim 17, wherein the detecting lens optical unit used in said detecting step has a deep focal depth such that the scattered light from floating foreign particles occurring over the entire region over said processed substrate, that is scanned by said intensity modulated beam, is imaged on the image plane.

19. A plasma processing method according to claim 17, wherein scattered light reflected from the walls of the processing chamber and brought to the plane of incidence by the detecting lens optical unit is blocked by a spatial filter in said detecting step.

20. A plasma processing method comprising:
an introduction step of introducing a processed substrate into a processing chamber;
a plasma generating step of generating plasma in said processing chamber;
a process step of processing said substrate by effecting a reaction of said substrate with said generated plasma in said processing chamber;
a foreign particle detection step of detecting foreign particles floating in or near said generated plasma in said processing chamber; and
a removal step of removing said substrate, which has undergone processing, from the processing chamber;
wherein said foreign particle detection step further comprises:
an irradiation step of irradiating a light beam, having a certain wavelength, an intensity of which is modulated with a prescribed frequency by an intensity modulator, inside said processing chamber through a window of the processing chamber, and scanning the laser beam in a plane substantially parallel to and above the substrate which substantially covers an entire surface of the substrate inside said processing chamber by using a scanning optical system;
a detecting step of detecting light that is scattered, as a result of the scanning of the laser beam, from foreign particles floating above the substrate, using a detecting lens optical unit having a wide view lens, which views the plane above the substrate and has a wide view angle substantially covering the area above the substrate through the window and has an optical axis different from an optical axis of the scanning optical system, and a sensor which receives a light having the certain wavelength separated from the scattered light passed through the wide view lens and outputs a first signal; and
a step of attaining floating foreign particle information by extracting from said first signal a signal component having the same frequency as said light, which was intensity modulated with the prescribed frequency.

21. A plasma processing method according to claim 20, wherein the detecting lens optical unit in the detecting step of said foreign particle detecting step has a deep focal depth for imaging on the image plane the scattered light from floating foreign particles occurring over the entire region over said processed substrate scanned by said intensity modulated beam.

22. A plasma processing method according to claim 20, wherein light reflected from the walls of the processing chamber and brought to the plane of incidence by the detecting lens is blocked by a spatial filter in said detecting step.

23. A plasma processing apparatus for process of a substrate, comprising:
a processing chamber provided with exhaust means for evacuating the interior thereof and for maintaining the processing chamber at a prescribed pressure;
gas supply means for supplying a desired gas to said processing chamber, the interior of which has been evacuated to vacuum with said exhaust means;
plasma generating means for generating plasma within said processing chamber in the state where the desired gas is supplied to the interior of said processing chamber by the gas supply means;
an illuminating optical system for irradiating and scanning a laser beam from outside said processing chamber, through a window in said processing chamber, in a plane substantially parallel to and above the substrate which substantially covers an entire surface of the substrate inside of said processing chamber, where plasma is being generated with the plasma generating means;
a detecting lens optical system for detecting, through said window, scattered light from foreign particles floating above the substrate within said processing chamber, by the irradiation and scanning of the laser beam with the illuminating optical system, the detecting optical system including a detecting lens optical unit having a wide view lens which views the plane above the substrate and which has a wide view angle substantially covering the area above the substrate; and
processing means for obtaining information on the state of the distribution of foreign particles floating inside said processing chamber by processing a signal attained by detecting scattered light from said floating foreign particles by the detecting optical system in synchronization with said laser beam scanning.

24. A plasma processing apparatus according to claim 23, wherein said processing chamber is provided with electrodes therein, and said plasma generating means generates plasma by high frequency discharge within said processing chamber by applying high frequency power to the electrodes in said processing chamber.

25. A plasma processing apparatus according to claim 24, wherein said illuminating optical system illuminates and scans the interior of said processing chamber with the laser beam, that is intensity modulated with a frequency different from the frequency of said high frequency power, through a window in said processing chamber.

26. A plasma processing apparatus according to claim 23, wherein said processing chamber is provided with a placement portion on which the substrate is placed, and said illuminating optical system scans the laser beam in the plane substantially parallel to and above the substrate so as to substantially cover the entire surface of the substrate placed on said placement portion.

27. A plasma processing apparatus according to claim 23, further comprising a display portion for displaying the results of processing with said processing means.

28. A plasma processing apparatus according to claim 27, wherein said display portion displays a representation of the distribution of the floating foreign particles within said processing chamber as results of processing by said processing means.

29. A plasma processing apparatus according to claim 23, wherein said detecting optical system includes means that detect, through the detecting lens optical unit, scattered light from foreign particles floating inside said processing chamber, by the illumination and scanning of the laser beam by said illuminating optical system.

30. A plasma processing apparatus according to claim 23, wherein said detecting optical system comprises a spatial filter for blocking scattered light reflected from the walls of the processing chamber impinging on said detecting lens optical unit.

31. A plasma processing apparatus according to claim 23, wherein said detecting lens optical unit has a deep depth of field as to form an image, at a plane of incidence without defocusing, of the scattered light from foreign particles within said processing chamber, occurring at any point between said detecting lens optical unit and the point at which foreign particle-scattered light occurs closest to said detecting lens optical unit within the region illuminated by said laser beam, and between said detecting lens optical unit and the point at which foreign particle-scattered light occurs farthest from said detecting lens optical unit within the region illuminated by said laser beam within said processing chamber.

* * * * *